(12) United States Patent
Breton et al.

(10) Patent No.: US 6,224,850 B1
(45) Date of Patent: *May 1, 2001

(54) ANTIWRINKLE COSMETIC/PHARMACEUTICAL COMPOSITIONS COMPRISING IRIDACEAE EXTRACTS

(75) Inventors: Lionel Breton, Versailles; Oliver De Lacharriere, Paris; Richard Martin, Rochecorbon, all of (FR)

(73) Assignee: Societe L'Oreal S.A., Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/826,424

(22) Filed: Mar. 27, 1997

(30) Foreign Application Priority Data

Mar. 27, 1996 (FR) .................................. 96 03817

(51) Int. Cl.⁷ .............................. A61K 9/00; A61K 7/00; A61K 35/78
(52) U.S. Cl. ................................ 424/47; 424/43; 424/59; 424/63; 424/195.1; 424/401; 514/725
(58) Field of Search ................. 424/401, 195.1, 424/47, 59, 63, 43; 514/725

(56) References Cited

FOREIGN PATENT DOCUMENTS 1-096 108 * 4/1989 (JP) .
7-196 472 * 8/1995 (JP) .
2 048 802 * 11/1995 (RU) .

OTHER PUBLICATIONS

Database WPI, Week 8717, Derwent Publications Ltd., London, GB; AN 87–118803 XP002021294: "Anti–ageing agent for treatment of rough skin—contains extract and/or solid material from iris etc" & JP–A–62 061 924 (Shiseido), Mar. 18, 1987.

Database WPI, Week 9250, Derwent Publications Ltd., London, GB; AN 92–410114 XP002021295: "Skin external moisture–retaining agent—contains extract from saffron extracted with e.g. water or ethanol" & JP–A–04 305 519 (Taisho Pharm), Oct. 28, 1992.

Database WPI, Week 9601, Derwent Publications Ltd., London, GB; AN 96–006882 XP002021296: "Cosmetics for maintaining skin moisture—comprise pptes. obtd. by extracting *Gardenia jasminoides* or *Crocus sativum* with water, treating extract and adjusting pH" & JP–A–07 285 845 (Pola Chem), Oct. 31, 1995.

Database WPI, Week 9530, Derwent Publications Ltd., London, GB; AN 95–228633 XP002021297: "Cell activator for preventing skin ageing—comprises *Belamcanda chinensis L.*, belonging to Iridaceaea or its dried roots extracts with e.g. water" & JP–A–07 138 179 (Ichimaru Pharcos), May 30, 1995.

Database WPI, Week 8652, Derwent Publications Ltd., London, GB; AN 86–341883 XP002021298: "External application agent or treating rough skin—contains pryidoxine or its deriv. and powder or extract or iris root" & JP–A–61 254 510 (Shiseido), Nov. 12, 1986.

* cited by examiner

Primary Examiner—Thurman K. Page
Assistant Examiner—Brian K. Seidleck
(74) Attorney, Agent, or Firm—Burns, Doane, Swecker & Mathis, L.L.P.

(57) ABSTRACT

Cosmetic/pharmaceutical compositions, well suited for the treatment of unwanted skin wrinkles, e.g., for visibly reducing human skin wrinkles, comprise an effective antiwrinkle amount of at least one extract of at least one member of the Iridaceae family that relaxes and/or loosens cutaneous and/or subcutaneous tissue, formulated into a cosmetically/pharmaceutically acceptable excipient or carrier therefor.

54 Claims, No Drawings

ANTIWRINKLE COSMETIC/PHARMACEUTICAL COMPOSITIONS COMPRISING IRIDACEAE EXTRACTS

BACKGROUND OF THE INVENTION

1. Technical Field of the Invention

The present invention relates to novel cosmetic/pharmaceutical compositions containing an effective amount of at least one extract of at least one Iridaceae, for loosening and/or relaxing the cutaneous and/or subcutaneous tissue, especially for treating (reducing or eliminating) normal and small (fine) skin wrinkles.

2. Description of the Prior Art

Women, or even men, today seek to maintain a youthful appearance for as long as possible and, consequently, seek to attenuate the signs of skin aging, which manifest themselves especially by normal and small wrinkles. In this regard, advertisements and fashion promote products intended to maintain a radiant skin for as long as possible and without wrinkles, which is the sign of a youthful skin, all the more so since physical appearance is important for peace of mind and/or for morale. Thus, it is important to feel physically and spiritually young.

To date, normal and small wrinkles were treated with cosmetic products containing active agents acting on the skin, for example by moisturizing it or by enhancing its cellular renewal or by promoting the synthesis of collagen which constitutes the cutaneous tissue. However, also to date, it was not known to this art how to treat wrinkles by acting on the muscular elements present in the skin.

It is known that the facial platysma muscles are under the control of the motor nerve afferences of the facial nerve and that, moreover, the interlobular septa of the hypodermis contain therein fibers which constitute a striated muscular tissue (*panniculus carnosus*). Too, it is also known that a subpopulation of fibroblasts of the dermis, designated myofibroblasts, exhibits characteristics which are common with the muscular tissue.

Prologue:

In the laboratories of the assignee hereof, in certain pathological and therapeutic conditions, the influence exerted on facial wrinkles by the nerves controlling all of this muscular tissue has been observed. Thus, in facial nerve conditions, in which the transmission of the nerve impulse is interrupted and/or reduced, there is observed in the area of innervation a paralysis of the facial muscles. This facial paralysis results, besides other clinical signs, in an attenuation, or even disappearance of the wrinkles.

In contrast, in the states of facial muscular hypercontraction, accentuation of facial wrinkles has also been observed. Furthermore, an accentuation of the facial wrinkles in the muscular hypertonia states in Parkinson's disease and side effects induced by neuroleptics too has been observed.

Moreover, it has been demonstrated that the botulinus toxin, originally used for treating spasms, is active on muscular spasticity states (see A. Blitzer et al., *Arch. Otolaryngol. Head Neck Surg.*, 119, pages 1018 to 1022 (1993)) and on the wrinkles on the glabella which are intersuperciliary wrinkles (see J. D. Carruters et al., *J. Dermatol. Surg. Oncol.*, 18, pages 17 to 21 (1992)). Consequently, it is possible to influence, via a pharmacological action, the nervous component of the wrinkles.

In the peripheral nervous system, the junction between a nerve and a muscle constitutes the neuromuscular plate, upstream of which there is the afferent nerve route denominated "motoneuron." Moreover, the cellular membranes of each nerve fiber comprise numerous ion channels, and especially chlorine channels, capable of permitting the corresponding element in ionic form, and in the case of the chlorine channels in chloride form, to pass therethrough. These channels are associated with neuronal receptors. The neuronal receptors associated at the periphery with the chlorine channels are especially receptors for glycine (glycine-strychnine sensitive receptors) and receptors for type A GABA (GABA-A receptors) (GABA=$\gamma$-aminobutyric acid).

It too is known that it is possible to reduce the excitability of the motoneuron by various pharmacological agents acting on the glycine-strychnine sensitive receptors or on the GABA-A receptors of the peripheral nervous system (see W. Sieghart, *Trends in Pharmacological Science*, December 1992, Vol. 131, pages 446 to 450). Thus, it is possible to modulate the excitability of the motoneuron, for example by glycine or gamma-aminobutyric acid (GABA).

The activation of these receptors opens the chlorine channels and permits entry of chloride ions, which results in an increase in the chloride ions in the cells of the nerve fiber and therefore to a hyperpolarization of the motoneurons which become, as a result, less excitable. This reduction in excitability of the motoneuron causes a lesser stimulation of the muscle fiber, thereby effecting its loosening.

SUMMARY OF THE INVENTION

After numerous clinical trials, it has now been determined that the contractile muscle fibers, in particular the striated muscle fibers, which are under the direct control of the neuromotor impulse, play an essential role in the pathogenicity of wrinkles and that the modulation of the neuromotor impulse attenuated not only the normal wrinkles, but also the small (fine) wrinkles and also exerted a "smoothing" effect on the cutaneous microrelief.

It has also now been determined that the cutaneous and subcutaneous tissues contained receptors associated with the chlorine channels, which, to date, had not been envisaged. It has therefore been found that it was possible to act on these channels in order to loosen or relax these tissues, and thus to reduce the normal and small wrinkles.

Also to date, no link had been established between the chlorine channels of the nerve fibers and wrinkles, and it was not considered to treat wrinkles by acting on the chlorine channels via activation of the receptors which are present in or close to these channels. Substances which may activate the receptors of the chlorine channels and therefore initiate the entry of chloride into the cells, are designated agonist substances.

Several receptors associated with the chlorine channel exist. These are especially the glycine-strychnine sensitive receptors and the GABA-A receptors, the latter themselves comprising several subunits including the GABA site, the benzodiazepine site, a type of steroid site and the site for the barbiturates. All of the substances or substrates which serve as agonists for these receptors or sites may be used to loosen or relax the cutaneous and/or subcutaneous tissues in accordance with the invention.

For a substance or species to be recognized as an agonist for the receptors of the chlorine channels, it must satisfy the following two requirements:

(a) be able to bind selectively to at least one of the different receptors associated with the chlorine channel;

(b) exert a relaxation effect on a contracted muscular tissue.

The first characteristic, which entails the possibility of binding to a receptor associated with a chlorine channel, does not permit distinguishing an agonist activity from an antagonist activity, but it makes it possible to define a potential affinity for the receptor.

The second characteristic permits selecting the agonists. The agonist activity of the substance studied may be demonstrated by the relaxation effect which it elicits on a muscular tissue which has been previously contracted by a chlorine channel antagonist substance. As chlorine channel antagonist substance, these may be selected from among known agents such as, and especially the following: bicuculline, strychnine, tert-butyl-bicyclophosphorothionate and picrotoxin.

Surprisingly, it has now been demonstrated that an extract of at least one Iridaceae satisfies the criteria for chlorine channel receptor agonist as defined above.

JP-A-60-201249 describes the use of Iridaceae extract for the treatment of rough skin by means of the dilatory activity of the blood vessels of the skin.

To the contrary, the present invention features antiwrinkle cosmetic/pharmaceutical compositions comprising an effective amount of an extract of at least one member of the Iridaceae family for relaxing and/or loosening the cutaneous and/or subcutaneous tissue.

The subject compositions are particularly effective for reducing normal and small (fine) wrinkles.

DETAILED DESCRIPTION OF BEST MODE AND SPECIFIC/PREFERRED EMBODIMENTS OF THE INVENTION

More particularly according to the present invention, the relaxation and/or loosening of the cutaneous and/or subcutaneous tissues is a muscular loosening or relaxation.

The compositions containing the extract according to the invention may be administered either locally, namely, topically, or by subcutaneous and/or intradermal injection, or systemically or generally, i.e., orally and/or by intramuscular injection.

The present invention also features a regimen for the cosmetic treatment of normal and/or small wrinkles, comprising applying topically, injecting or ingesting a composition comprising an effective amount of an extract of at least one Iridaceae.

The extract of at least one Iridaceae may be any extract prepared or recovered from plant material derived from the Iridaceae family.

The compositions may contain an extract of at least one Iridaceae obtained from plant material derived from whole plant cultured in vivo or derived from in vitro culture.

The selection pressure exerted by the physicochemical conditions during the growth of the plant cells in vitro permits obtaining a standardized plant material available throughout the year, as opposed to plants cultured in vivo.

By "in vitro" culture is intended all techniques known to this art which permit artificially producing a plant or a portion of a plant.

There may thus be used, for example, according to the invention, an extract of roots of at least one Iridaceae cultured in vitro or an extract of undifferentiated cells of at least one Iridaceae.

Preferably, an extract is used which is obtained from plant material cultured in vitro and, even more preferably, an extract obtained from undifferentiated cells cultured in vitro.

By "undifferentiated plant cell" is intended any plant cell exhibiting none of the traits of a specific specialization and capable of living by itself and not in dependency on other cells. These undifferentiated plant cells are possibly capable, under the effect of induction, of any differentiation in conformity with their genome.

According to the technique of culture selected, and in particular according to the culture medium selected, it is possible to obtain, from the same explant, undifferentiated plant cells having different traits.

The Iridaceae (or Iris) family comprises about 750 species.

Plants of the Iridaceae family are especially useful for their aromatic and ornamental properties.

Among the Iridaceae genera which are suitable according to the invention, representative thereof, for example, are the genera Romulea, Crocus, Iris, Gladiolus, Sisyrinchium or Hermodactylus.

Exemplary plant materials are those obtained from *Iris germanica, Iris florentina, Iris pallida, Crocus versicolor, Romulea bulbucodium* or *Gladiolus communis*.

More particularly according to the invention, a plant material derived from the genus Iris and preferably plant material from *Iris pallida* is employed.

Any extraction technique known to this art may be used to prepare the Iridaceae extract contained in the composition according to the invention.

Particularly exemplary extracts are alcoholic, especially ethanolic or aqueous/alcoholic extracts.

An Iridaceae extract prepared by the technique described in French patent application No. 95-02379, assigned to the assignee hereof, may also be used.

Thus, in a first stage, the plant material is ground in an aqueous solution at cold temperature, in a second stage the particles in suspension are removed from the aqueous solution obtained from the first stage, and in a third stage, the aqueous solution derived from the second stage is sterilized. This aqueous solution corresponds to the extract.

Moreover, the first stage may advantageously be replaced by a simple operation of freezing the plant tissues (for example at −20° C.), followed by an aqueous extraction in which the second and third stages described above are repeated.

One example of preparation of Iridaceae extract which may be used according to the invention is in fact set forth in the examples below.

The effective amount of Iridaceae extract contained in the compositions of the invention is of course dependent on the desired effect and may therefore vary to a great extent.

To provide an order of magnitude, if the composition is a cosmetic composition, it may contain an extract of at least one Iridaceae in an amount constituting from 0.01% to 20% of the total weight of the composition and, preferably, in an amount constituting from 0.1% to 5% of the total weight of the composition.

Also to provide an order of magnitude, if the composition is a pharmaceutical composition, it may contain an extract of at least one Iridaceae in an amount constituting from 0.01% to 30% of the total weight of the composition and, preferably, in an amount constituting from 0.1% to 10% of the total weight of the composition.

The compositions according to the invention may be provided in all of the galenic or dosage forms normally used for topical, injectable or oral application.

The amounts of the different constituents of the compositions according to the invention are those conventionally used in the fields considered and are appropriate for their galenic form.

For topical application, the compositions of the invention comprise a medium which is compatible with water. These compositions may be provided, especially, in the form of aqueous, alcoholic or aqueous/alcoholic solutions, of gels, of lotions, of ointments, of water-in-oil or oil-in-water emulsions having the appearance of a cream or of a gel, of microemulsions, of aerosols, or in the form of vesicular dispersions containing ionic and/or nonionic lipids. These dosage forms are formulated according to the customary methods in the fields under consideration.

The compositions for topical application may advantageously constitute a cosmetic or pharmaceutical composition for protection, treatment or care of the face, the neck, the hands or the body, (for example day creams, night creams, sunscreen creams or oils, lotions, body milks), a makeup composition (for example foundation) or a composition for artificial tanning.

When the composition of the invention is an emulsion, the proportion of fatty phase which it contains may range from 5% to 80% by weight, preferably from 5% to 50% by weight relative to the total weight of the composition. The fats and the emulsifiers present in the composition in emulsion form are selected from among those conventionally used in the cosmetic or pharmaceutical field.

Exemplary fats include the mineral oils (petroleum jelly), vegetable oils (liquid fraction of shea butter) and hydrogenated derivatives thereof, animal oils, synthetic oils (perhydrosqualene), silicone oils (dimethylpolysiloxane) and fluorinated oils. Other fats include the fatty alcohols (cetyl alcohol, stearyl alcohol), the fatty acids (stearic acid) and the waxes.

The emulsifiers may be present in the composition in a proportion ranging from 0.3% to 30% by weight, preferably from 0.5% to 30% by weight relative to the total weight of the composition.

In known fashion, the cosmetic or pharmaceutical compositions of the invention may also contain customary additives and adjuvants in the corresponding fields, such as hydrophilic or lipophilic gelling agents, preservatives, antioxidants, solvents, perfumes, fillers, UV-screening agents and colorants. Moreover, these compositions may contain hydrophilic or lipophilic active agents. The amounts of these different additives and adjuvants or active agents are those conventionally used in the cosmetic or pharmaceutical field, and range, for example, from 0.01% to 20% of the total weight of the composition. These adjuvants/additives or these active agents, depending on their particular nature, may be introduced in the fatty phase, in the aqueous phase and/or in the lipid vesicles.

Exemplary active agents which may be formulated into the compositions of the invention include, especially, the active agents having a beneficial effect for the treatment of normal or small wrinkles, and in particular keratolytic active agents. By "keratolytic" is intended an active agent having desquamating, peeling or scrubbing properties, or an active agent capable of softening the stratum corneum.

Exemplary active agents which are effective for reducing normal or small wrinkles include, in particular, the hydroxy acids and the retinoids.

Representative hydroxy acids include, for example, α-hydroxy acids or β-hydroxy acids, which may be linear, branched or cyclic, saturated or unsaturated. The hydrogen atoms of the carbon chain may, in addition, be substituted with halogens, halogenated, alkylated, acylated, acyloxylated, alkoxycarbonylated or alkoxylated radicals having from 2 to 18 carbon atoms.

The hydroxy acids which are especially suitable include glycolic, lactic, malic, tartaric, citric, 2-hydroxyalkanoic, mandelic and salicylic acids, as well as the alkylated derivatives thereof such as n-octanoyl-5-salicylic acid, n-dodecanoyl-5-salicylic acid, n-decanoyl-5-salicylic acid, n-octyl-5-salicylic acid, n-heptyloxy-5 or -4-salicylic acid, 2-hydroxy-3-methylbenzoic acid, or their alkoxylated derivatives such as 2-hydroxy-3-methoxybenzoic acid.

The retinoids which are especially suitable include retinoic acid (all-trans or 13-cis) and derivatives thereof, retinol (vitamin A) and its esters such as retinol palmitate, retinol acetate and retinol propionate, as well as their salts.

These active agents are advantageously present in concentrations ranging from 0.0001% to 5% by weight relative to the total weight of the composition.

When the compositions of the invention are formulated for application via the oral route, they are provided in the galenic forms which are customary therefor, such as tablets, gelatin capsules, oral products, especially prepared immediately before use, granules, powders, in the customary excipients or carriers for such an application.

When the compositions of the invention are formulated to be injected, they may be provided in the form of solutions containing the excipients customarily used for injections, for example in the form of an isotonic solution of sodium chloride.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Preparation of an *Iris pallida* Extract

Undifferentiated *Iris pallida* cells cultured in vitro under axenic conditions were recovered after culture in an Erlenmeyer flask or in a fermenter by filtration on a 50 μm screen. 27.5 ml of demineralized water were added to 55 g of fresh material thus obtained. The entire mass was ground in a Turax blender at 24,000 rpm for 1 minute at 4° C. (ice bath). The ground product was centrifuged at 15 to 10,000 G at 4° C. The supernatant was filtered at 0.22 μm (sterilizing filtration).

The extract thus prepared was stored at 4° C. It contained about 15 g of dry matter per liter.

If the plant material was the whole plant, the fresh material to be treated was provided according to the dry weight such as to be under the same extraction conditions as in vitro. The different parts of the plant were collected according to the relative weight of each part thereof. The cold treatment made it possible to freeze the enzymatic activities, the sterilizing filtration avoided the degradation of the active agents by environmental microorganisms. Finally, the water vehicle was compatible with the receptors ex vivo and facilitated the cosmetic or pharmaceutical formulations.

EXAMPLE 2

Measurement of the Affinity of the *Iris pallida* Extract for the Glycine and GABA-A Receptors (type A Receptor for γ-aminobutyric Acid)

The affinity for the glycine receptors was determined according to the technique described by Marvizon and colleagues in *Mol. Pharmacol.*, 30, pp. 590–597 (1986). The affinity for the GABA-A receptors was determined according to the technique described by Snodgrass, S. R., *Nature*, 273, 392 (1978).

Summary of the Experimental Conditions

Glycine Receptor:

The displacement of tritiated strychnine bound to the glycine receptor was measured by prior incubation of 2 nM of tritiated strychnine with rat spinal cord membranes for 10 minutes at 0° C.

The *Iris pallida* extract was tested at 1% and 5% of its initial concentration. The $IC_{50}$ of the strychnine (dose necessary to displace 50% of the tritiated strychnine bound to the receptor) was measured by displacement by nonlabelled strychnine.

GABA-A Receptor:

The displacement of tritiated muscimol bound to the GABA-A receptor was measured by prior incubation of 2.5 nM of tritiated muscimol with rat cerebral cortex for 10 minutes at 4° C.

The *Iris pallida* extract was tested at 1% and 5% of its initial concentration.

The $IC_{50}$ of the muscimol (dose necessary to displace 50% of the tritiated muscimol bound to the receptor) was measured by displacement by nonlabelled muscimol.

The results obtained, expressed as percentage inhibition of binding of the radioactive ligand, are reported in the following Table I:

TABLE 1

| *Iris* pallida extract (concentration) | 1% | 5% |
|---|---|---|
| Glycine receptor | 71 | 92 |
| GABA-A receptor | 100 | 100 |
| Reference: strychnine (glycine) | $IC_{50}$:26.9 nM | |
| Reference: muscimol (GABA-A) | $IC_{50}$:8.2 nM | |

These results evidence that the *Iris pallida* extract was a good ligand for the glycine and GABA-A receptors.

The relationship existing between these receptors, the chlorine channels and the muscle contractions makes the *Iris pallida* extract a good antiwrinkle agent.

EXAMPLE 3

Measurement of the Effect of *Iris pallida* Extract on the Delay in the Appearance of a Chlorine Channel Antagonist Effect (convulsions) Induced by Strychnine in Mice After Subcutaneous Administration The measurement was carried out according to the technique described by Krall and colleagues, Epilepsia, 19, 409–428 (1978).

The *Iris pallida* extract was administered subcutaneously in a volume of 10 ml/kg, at the desired doses. 30 minutes after treatment, a solution of strychnine was injected subcutaneously at the dose of 1 mg/kg. The vehicle was sterile water.

The appearance of convulsions was observed for 30 minutes after the injection of strychnine. The delay in the appearance of the convulsions was also measured.

The reference compound was Diazepam at 3 mg/kg.

The results obtained are reported in the following Table II. The delay in the appearance of the convulsions is expressed in seconds. The values reported are the mean values of the delays measured per animal in each group.

TABLE II

| Product | Delay | Variation (%) |
|---|---|---|
| Vehicle | 266 | |
| Diazepam | 3431 | +1190 |
| *Iris* pallida (1 ml/kg) | 333 | +25 |
| *Iris* pallida (5 ml/kg) | 321 | +21 |

The *Iris pallida* extract exerted, by retarding the time of appearance of the convulsions, a relaxing effect which made it an antiwrinkle active agent.

EXAMPLE 4

Specific Examples of Compositions According to the Invention

Composition 1: Care Lotion for the Face:

| | |
|---|---|
| Extract of Example 1 | 7.00% |
| Antioxidant | 0.05% |
| Preservative | 0.30% |
| Ethanol (solvent) | 8.00% |
| Water | qs 100% |

The lotion obtained was effective on wrinkles during repeated use (twice daily application for one month).

Composition 2: Face Care Gel:

| | |
|---|---|
| Extract of Example 1 | 7.00% |
| Hydroxypropyl cellulose* | 1.00% |
| Preservative | 0.30% |
| Ethanol (solvent) | 15.00% |
| Antioxidant | 0.05% |
| Water | qs 100% |

*: Klucel H marketed by Hercules (gelling agent).

The gel obtained is effective on wrinkles. It may be applied daily, morning and evening, for one month.

Composition 3: Face Care Cream (oil-in-water emulsion):

| | |
|---|---|
| Extract of Example 1 | 5.00% |
| Glycerol stearate (emulsifier) | 2.00% |
| Polysorbate 60 (Tween 60 marketed by ICI) (emulsifier) | 1.00% |
| Stearic acid | 1.40% |
| Triethanolamine (neutralizing agent) | 0.70% |
| Carbomer (Carbopol 940 marketed by Goodrich) | 0.40% |
| Liquid fraction of shea butter | 12.00% |
| Perhydrosqualene | 12.00% |
| Preservative | 0.30% |
| Perfume | 0.50% |
| Antioxidant | 0.05% |
| Water | qs 100% |

A white unctuous cream was obtained which is active on normal and small (fine) wrinkles, and which may be applied daily.

Composition 4: Face Care Cream (oil-in-water emulsion):

| | |
|---|---|
| Extract of Example 1 | 5.00% |
| Glycerol mono-, distearate | 2.00% |
| Cetyl alcohol | 1.50% |
| Cetylstearyl alcohol/oxyethylated cetylstearyl alcohol mixture 33 EO | 7.00% |
| Dimethylpolysiloxane | 1.50% |
| Petroleum jelly | 17.50% |
| Preservative | 0.30% |
| Perfume | 0.50% |
| Glycerin | 12.50% |
| Water | qs 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic or pharmaceutical composition suited for the treatment of unwanted skin wrinkles, comprising an amount sufficient to relax and/or loosen cutaneous or subcutaneous muscle tissue, thereby effectively reducing unwanted skin wrinkles of at least one extract of at least one member of the Iridaceae family, wherein said Iridaceae extract specifically binds glycine or GABA-A receptors that relaxes and/or loosens cutaneous and/or subcutaneous tissue, formulated into a cosmetically/pharmaceutically acceptable excipient or carrier therefor.

2. The cosmetic or pharmaceutical composition as defined by claim 1, said effective anti-wrinkle amount being sufficient to attenuate or result in the disappearance of wrinkles.

3. The cosmetic or pharmaceutical composition as defined by claim 1, formulated as a dosage form suited for topical application.

4. The cosmetic or pharmaceutical composition as defined by claim 1, formulated as a dosage form suited for oral administration.

5. The cosmetic or pharmaceutical composition as defined by claim 1, formulated as a dosage form suited for injectable administration.

6. The cosmetic or pharmaceutical composition as defined by claim 1, said at least one extract comprising a whole plant extract.

7. The cosmetic or pharmaceutical composition as defined by claim 1, said at least one extract comprising a extract plant materials obtained via in vitro culture.

8. The cosmetic or pharmaceutical composition as defined by claim 7, said plant material having been obtained via in vitro culture of undifferentiated cells.

9. The cosmetic or pharmaceutical composition as defined by claim 1, said at least one extract being of at least one Iridaceae of at least one of the genera Romulea, Crocus, Iris, Gladiolus, Sisyrinchiun and Hermodactylus.

10. The cosmetic or pharmaceutical composition as defined by claim 9, said at least one extract being of at least one Iridaceae of the genus Iris.

11. The cosmetic or pharmaceutical composition as defined by claim 10, said at least one extract comprising an *Iris pallida* extract.

12. The cosmetic or pharmaceutical composition as defined by claim 1, said at least one extract comprising from 0.01% to 20% by weight thereof.

13. The cosmetic or pharmaceutical composition as defined by claim 12, said at least one extract comprising from 0.1% to 5% by weight thereof.

14. The cosmetic or pharmaceutical composition as defined by claim 1, said at least one extract comprising from 0.01% to 30% by weight thereof.

15. The cosmetic or pharmaceutical composition as defined by claim 14, said at least one extract comprising from 0.1% to 10% by weight thereof.

16. The cosmetic or pharmaceutical composition as defined by claim 1, comprising a solution, gel, ointment, lotion, emulsion, cream, microemulsion, aerosol, dispersion or milk.

17. The cosmetic or pharmaceutical composition as defined by claim 1, further comprising at least one hydrophilic or lipophilic gelling agent, preservative, antioxidant, solvent, perfume, filler, UV-screening agent and/or colorant.

18. The cosmetic or pharmaceutical composition as defined by claim 1, further comprising at least one other hydrophilic and/or lipophilic bioactive agent.

19. The cosmetic or pharmaceutical composition as defined by claim 18, said at least one other bioactive agent comprising an antiwrinkle bioactive agent.

20. The cosmetic or pharmaceutical composition as defined by claim 19, said at least one other bioactive agent comprising a keratolytic active agent, a hydroxy acid and/or a retinoid.

21. A method for reducing unwanted human skin wrinkles, comprising administering to an individual in need of such treatment an anti-wrinkle effective amount of the cosmetic or pharmaceutical composition as defined by claim 1, for such period of time to relax or loosen cutaneous or subcutaneous muscle tissue, thereby resulting in the attenuation or disappearance of said unwanted skin wrinkles.

22. The method as defined by claim 21, which visibly attenuates or results in the disappearance of human skin wrinkles.

23. The method as defined by claim 21, comprising topically applying said cosmetic or pharmaceutical composition to an afflicted skin area of said individual.

24. The cosmetic or pharmaceutical composition of claim 1, wherein said Iridaceae extract specifically binds glycine or GABA-A receptors.

25. The method of claim 21, wherein said Iridaceae extract specifically binds glycine or GABA-A receptors.

26. A cosmetic or pharmaceutical composition suited for the treatment of unwanted skin wrinkles, comprising an amount sufficient to relax and/or loosen cutaneous or subcutaneous muscle tissue, thereby effectively reducing unwanted skin wrinkles of at least one extract of 0.01 to 30% by weight of at least one member of the Iridaceae family that relaxes and/or loosens cutaneous and/or subcutaneous tissue, formulated into a cosmetically/pharmaceutically acceptable excipient or carrier therefor.

27. The cosmetic or pharmaceutical composition as defined by claim 26, said effective anti-wrinkle amount being sufficient to attenuate or result in the disappearance of wrinkles.

28. The cosmetic or pharmaceutical composition as defined by claim 26, formulated as a dosage form suited for topical application.

29. The cosmetic or pharmaceutical composition as defined by claim 26, formulated as a dosage form suited for oral administration.

30. The cosmetic or pharmaceutical composition as defined by claim 26, formulated as a dosage form suited for injectable administration.

31. The cosmetic or pharmaceutical composition as defined by claim 26, said at least one extract comprising a whole plant extract.

32. The cosmetic or pharmaceutical composition as defined by claim 26, said at least one extract comprising a extract plant materials obtained via in vitro culture.

33. The cosmetic or pharmaceutical composition as defined by claim 32, said plant material having been obtained via in vitro culture of undifferentiated cells.

34. The cosmetic or pharmaceutical composition as defined by claim 26, said at least one extract being of at least one Iridaceae of at least one of the genera Romulea, Crocus, Iris, Gladiolus, Sisyrinchium and Ilermodactylus.

35. The cosmetic or pharmaceutical composition as defined by claim 34, said at least one extract being of at least one Iridaceae of the genus Iris.

36. The cosmetic or pharmaceutical composition as defined by claim 35, said at least one extract comprising an *Iris pallida* extract.

37. The cosmetic or pharmaceutical composition as defined by claim 26, said at least one extract comprising from 0.01% to 20% by weight thereof.

38. The cosmetic or pharmaceutical composition as defined by claim 37, said at least one extract comprising from 0.1% to 5% by weight thereof.

39. The cosmetic or pharmaceutical composition as defined by claim 26, said at least one extract comprising from 0.01% to 30% by weight thereof.

40. The cosmetic or pharmaceutical composition as defined by claim 39, said at least one extract comprising from 0.1% to 10% by weight thereof.

41. The cosmetic or pharmaceutical composition as defined by claim 26, comprising a solution, gel, ointment, lotion, emulsion, cream, microemulsion, aerosol, dispersion or milk.

42. The cosmetic of pharmaceutical composition as defined by claim 26, further comprising at least one hydrophilic or lipophilic gelling agent, preservative, antioxidant, solevent, perfume, filler, UV-screeing, agent and/or colorant.

43. The cosmetic of pharmaceutical composition as defined by claim 26, further comprising at least one other hydrophilic and/of lipophilic bioactive agent.

44. The cosmetic of pharmaceutical composition as defined by claim 43, said at least one other bioactive agent comprising an antiwrinkle bioactive agent.

45. The cosmetic or pharmaceutical composition as defined by claim 44, said at least one other bioactive agent comprising a keratolytic active agent, a hydroxy acid and/or a retinoid.

46. A method for reducing unwanted human skin wrinkles, comprising administering to an individual in need of such treatment an anti-wrinkle effective amount of the cosmetic or pharmaceutical composition as defined by claim 26, for such period of time to relax or loosen cutaneous or subcutaneous muscle tissue, thereby resulting in the attenuation or disappearance of said unwanted skin wrinkles.

47. The method as defined by claim 46, which visibly attenuates or results in the disappearance of human skin wrinkles.

48. The method as defined by claim 46, comprising topically applying said cosmetic or pharmaceutical composition to an afflicted skin area of said individual.

49. The cosmetic or pharmaceutical composition of claim 26, wherein said Iridaceae extract specifically binds glycine or GABA-A receptors.

50. The method of claim 46, wherein said Iridaceae extract specifically binds glycine or GADA-A receptors.

51. A method for reducing unwanted human skin wrinkles, comprising administering to an individual in need of such treatment an anti wrinkle effective amount of the cosmetic or pharmaceutical composition suited for the treatment of unwanted skin wrinkles, comprising an amount sufficient to relax and/or loosen cutaneous or subcutaneous muscle tissue, thereby effectively reducing unwanted skin wrinkles of at least one extract of at least one member of the Iridaceae family, for such period of time to relax or loosen cutaneous or subcutaneous mussle tissue, thereby resulting in the attenuation or disappearance of said unwanted skin wrinkles.

52. The method as defined by claim 51, which visibly attenuates or results in the disappearance of human skin wrinkles.

53. The method as defined by claim 51, comprising topically applying said cosmetic or pharmaceutical composition to an afflicted skin area of said individual.

54. The method of claim 51, wherein said Iridaceae extract specifically binds glycine or GABA-A receptors.

* * * * *